(12) United States Patent
Haidukewych (10) Patent No.: US 9,408,612 B2
(45) Date of Patent: Aug. 9, 2016

(54) FRACTURE ALIGNMENT DEVICE

(76) Inventor: George J. Haidukewych, Orlando, FL (US)

( * ) Notice: Subject to any disclaimer, the term of this patent is extended or adjusted under 35 U.S.C. 154(b) by 0 days.

(21) Appl. No.: 13/373,561

(22) Filed: Nov. 18, 2011

(65) Prior Publication Data

US 2013/0125903 A1    May 23, 2013

(51) Int. Cl.
| | |
|---|---|
| *A61F 5/00* | (2006.01) |
| *A61B 17/135* | (2006.01) |
| *A61F 5/058* | (2006.01) |
| *A61B 17/00* | (2006.01) |
| *A61F 7/00* | (2006.01) |

(52) U.S. Cl.
CPC ........... *A61B 17/135* (2013.01); *A61F 5/05816* (2013.01); *A61F 5/05825* (2013.01); *A61B 2017/00539* (2013.01); *A61F 2007/0029* (2013.01); *A61F 2007/0039* (2013.01); *A61F 2007/0054* (2013.01)

(58) Field of Classification Search
CPC ............. A61B 2017/00539; A61B 2007/0029; A61B 2007/0039; A61B 5/05816; A61B 2007/0091; A61B 5/05841; A61B 5/0585; A61B 5/05858

USPC ............ 602/39, 32, 13, 5, 6, 36; 128/DIG. 20
See application file for complete search history.

(56) References Cited

U.S. PATENT DOCUMENTS

| | | | | |
|---|---|---|---|---|
| 4,928,677 | A | * | 5/1990 | Barber ............................ 602/21 |
| 5,409,451 | A | * | 4/1995 | Daneman ........................ 602/21 |
| 8,096,964 | B1 | * | 1/2012 | Bruehwiler et al. ............ 602/13 |
| 2012/0253250 | A1 | * | 10/2012 | Spahn et al. .................... 602/13 |

\* cited by examiner

*Primary Examiner* — Victoria J Hicks (57) ABSTRACT

A fracture alignment device to immobilize a patient's limb during a surgical procedure having an inner flexible layer and an outer flexible layer of fluid impervious material each including a central major portion or body having a plurality of lateral minor extensions or fingers extending outwardly therefrom to form a fluid tight chamber coupled to a pressure regulator to control the pressure within the fluid tight chamber and an alignment retainer to position and maintain the inner flexible layer in contact with the patient's limb when the pressure within the fluid tight chamber is sufficiently different from the ambient pressure outside the fluid tight chamber to immobilize the patient's limb.

5 Claims, 9 Drawing Sheets

FRACTURE ALIGNMENT DEVICE

BACKGROUND OF THE INVENTION

1. Field of the Invention

A fracture alignment device to immobilize a patient's limb during a surgical procedure.

2. Description of the Prior Art

There is present need to stabilize a fractured arm or leg to allow a surgeon ready access to the injured limb during a surgical procedure.

The following examples fall short in one or more aspects dictated by such medical situations.

U.S. Pat. No. 6,318,372 discloses a vacuum activated veterinary surgical positioning system for supporting and retaining the body of a four-legged animal in a selected position. The system includes a bag made of flexible, air impermeable material having top and bottom opposing walls air impermeably joined at their upper, lower and lateral edges. A charge of elastically deformable plastic beads is disposed within the bag. A valve communicating with the interior of the bag is provided for evacuating air therefrom to cause the beads to interengage to form a rigid structure and immobilize the animal's trunk in the selected position when the bag is firmly packed against the trunk. Finally, a strap is attached to each of the corners of the bag for attachment to each of the animal's legs to retain the leg in a desired position.

U.S. Pat. No. 6,226,820 teaches a gel pad assembly comprising a flexible gel pad and an adjustable shape retainer integral with the gel pad. A flexible first outer wall cooperates with a flexible inner wall to form a first chamber. A gel is located within the first chamber. A flexible second outer wall cooperates with the inner wall to form a second chamber coextensive with the first chamber. The integral shape retainer is located within the second chamber and is selectively adjustable between a flexible condition wherein the flexible walls are conformable to a variety of desired shapes and a rigid condition wherein the flexible walls are retained in a selected one of the desired shapes.

U.S. Pat. No. 5,121,756 shows a vacuum immobilizer support comprising an elongated, flexible casing having neck, thoracic and pelvic regions. An evacuation valve is provided to allow the casing to be converted from a flexible state to an evacuated state. Stiffener sections are provided in the casing to prevent transverse bending of the casing in the neck, thoracic and pelvic regions. The stiffener sections allow transverse bending along an axis between the thoracic and pelvic regions. An intermediate stiffener section is provided to prevent longitudinal shortening of the casing between upper and lower stiffener sections. Discrete elements are disposed within the casing and allow the casing to conform to a patient when in its flexible state and to be rigidly fixed when in its evacuated state.

U.S. Pat. No. 6,793,639 describes a pelvic splint for immobilizing and maintaining the annular integrity of the pelvis in the event of a pelvic ring fracture extending from the iliac crest down to about the middle third of the thighs and substantially encircles the pelvis of the victim. The splint is secured about the pelvis of the victim with two or more adjustable straps. The splint comprises a flexible casing having at least one pliable padding layer disposed therein and a plurality of flexible members individually disposed in pockets spaced apart about the casing. Once tightly secured around the pelvis by the adjustable straps, the splint conforms to the contours of the victim's pelvic area and stabilizes the pelvis by preventing lateral movement and constraining the pelvis in such a manner to preserve the annular integrity thereof.

U.S. Pat. No. 4,378,009 shows a brace comprising an elongated, elastic tube to a person's knee or other part of the body. The brace is wrapped about the knee in a criss-cross fashion wherein four diagonal members intersect at four points surrounding the knee cap, i.e., top, bottom and each side. The brace is held in place by tape, velcro or other fastening means. The brace may be solid or inflated with air or another suitable fluid until a comfortable, protective pressure is reached within the elongated tube. When properly positioned and filled, the brace supports the knee or other body member.

U.S. Pat. No. 5,435,009 relates to an inflatable garment applying compression to a limb for the treatment of vascular disorders. The garment is made with an inflatable chamber of superimposed layers of sheet material. Side portions of the blank are joined together in the garment to encompass the foot. An inflatable tongue is located to lie under the foot. The side portions of the blank and the tongue form intercommunicating inflatable sacs. The tongue itself is not laterally joined to the side portions of the blank.

U.S. Pat. No. 5,569,176 teaches a cervical traction and exercise device secured about the head and neck for imparting the desired lordotic shape into the cervical region of the spine and manipulating the spine and surrounding tissue to promote fluid and cellular exchange in and around the intervertebral discs. The device includes a frame, an upstanding neck support carried by the frame, an inflatable elongated bladder carried by the neck support, restraining straps for securing the device to the user's head such that the bladder is disposed below and adjacent the user's neck, and means for selectively inflating and deflating the bladder to force the cervical spine to curve forwardly and apply angular traction to the spine.

U.S. Pat. No. 6,306,112 discloses a therapeutic ankle support brace bladder pad member including an inflated air support pocket and a second support pocket containing gel material. An overlay fabric material is integrally attached to the bladder to provide additional support and enables removable attachment of the bladder to side support members of a therapeutic brace.

U.S. Pat. No. 6,918,393 relates to a device for supporting and stabilizing an injured person. Comprising a flexible film element whose two films define an air-tight inner space can be evacuated and in which loose particle-containing chambers are provided. The device comprises a torso part and a head part that is provided on both sides with shoulder rests.

U.S. Pat. No. 7,771,376 shows a massage device for massaging comprising an inflatable garment having a plurality of inflation bladders to apply pressure to a body part and an inflation assembly includes a manifold into which the pressurized fluid flows. A plurality of inflation valves control the flow of fluid from the manifold to the bladders. A manifold valve controls the maximum pressure level within the bladders. The inflation assembly may have a predeterminated inflation capacity which defines a maximum bladder size as well as an array in which the bladders are arranged.

U.S. Pat. No. 7,871,387 describes a compression apparatus comprising a sleeve configured for disposal about a limb. The sleeve comprises a first portion defining a first expandable chamber and a second portion defining a second expandable chamber and a third expandable chamber. The second portion includes a connector in fluid communication with a pressurized fluid source and the chambers thereby facilitating fluid communication between the pressurized fluid source and the chambers. The first portion is removable from the second portion. The first portion may be connected to the second portion through a perforated attachment.

US 2006/0189907 relates to a soft, light-weight brace for a patient's limb PL to provide prophylactic support to a patient while allowing the patient mobility. The brace may be adjustable and configured to be fitted to patients having limbs of differing sizes to allow the patient to obtain a more closely fitted brace.

US 2007/0161933 teaches a garment comprising at least one inflatable chamber for applying compression to a limb for assisting venous return and an elevation member to elevate the limb. The elevation member may comprise an inflatable chamber.

US 2007/0249977 shows a pressurized medical device comprising an inflatable element to contact a part of a patient; a fluid connector attached to the element to deliver fluid to the element; a control system to control flow of fluid in the device; a first element pressure sensor to measure the pressure exerted by the element on the part of the patient and detection means to detect malfunctioning of the first element pressure sensor.

US 2008/0004555 disclosed is a medical device that operates as a supporting splint for the limbs and other body parts necessary for the treatment of a variety of medical and surgical conditions comprising an inflatable, flexible, lightweight water-resistant splint whose measure of rigidity is easily controlled by the fitter or user. The device is designed to allow normal blood circulation to the treated body part, provide ventilation to the area, enable easy inspection of an injury and allow partial movement of the treated part.

Additional examples of the prior art are found in the following patent documents: U.S. Pat. No. 2,110,414: U.S. Pat. No. 3,299,888: U.S. Pat. No. 4,355,632: U.S. Pat. No. 4,407,277: U.S. Pat. No. 4,620,698: U.S. Pat. No. 4,747,400: U.S. Pat. No. 5,042,508: U.S. Pat. No. 5,207,688: U.S. Pat. No. 5,207,716: U.S. Pat. No. 5,305,750: U.S. Pat. No. 5,328,445: U.S. Pat. No. 5,350,378: U.S. Pat. No. 5,577,998: U.S. Pat. No. 6,656,143: U.S. Pat. No. 7,343,916: U.S. Pat. No. 7,665,167: US 2004/0010212: US 2009/0062703: US 2009/017222: US 2009/0312681: US 2010/0100018: US 2010/0249679: US 2011/0028873 and Des. 217,892.

SUMMARY OF THE INVENTION

The present invention relates to a fracture alignment device to immobilize a patient's limb without the necessity of using straps while allowing access to a surgical site during a surgical procedure. The fracture alignment device comprises two flexible layers of fluid impervious material cooperatively forming a fluid tight enclosure or chamber coupled to a pressure regulator to control the pressure within the fluid tight chamber in combination with an alignment retainer to position and maintain one of the flexible layers of fluid impervious material in contact with the patient's limb.

The alignment retainer may comprise a pliable or malleable metal or formable thermoplastic in the form of a frame, sheet or slats, or a plurality of beads, pellets or similar relatively small particulate material. The pressure regulator may comprise a positive pressure pump device or a vacuum pump device to create a pressure differential between the ambient atmosphere and the interior fluid tight enclosure or chamber depending on the type of alignment retainer employed.

More specifically, the fracture alignment device comprises an inflatable fluid tight enclosure or bladder and an alignment retainer.

The inflatable fluid tight enclosure or bladder is coupled to a fluid pressure regulator to supply fluid to the interior of the inflatable fluid tight enclosure or bladder to selectively inflate the inflatable fluid tight enclosure or bladder. The fluid pressure regulator may comprise an air or gas pump or pressurized air or gas tank or similar air supply control or a manual air bulb to selectively pressurize or inflate the inflatable fluid tight enclosure or bladder and a pressure relief valve to selectively relieve the internal pressure from the interior of the inflatable fluid tight enclosure or bladder to deflate the inflatable fluid tight enclosure or bladder into an ambient state or condition after use.

The flexible layers comprise a central major portion having a plurality of lateral retainer extensions or fingers extending outwardly therefrom to engage and immobilize the patient's limb when the inflatable fluid tight enclosure or bladder is inflated or in an immobilization state or condition.

The alignment retainer may comprise pliable or malleable wire-like elements of metal or other suitable material that can be bent or formed to follow the contour of the patient's limb to at least partially encircle the patient's limb in an operative position such that the central major portion and the lateral retainer extensions or fingers are held in position to engage the patient's limb when the inflatable fluid tight enclosure or bladder is inflated to immobilize the patient's limb. Of course, the alignment retainer may comprise a plate or sheet of pliable or malleable material or a plurality of strips, slats or ribs of pliable or malleable material extending transversely or laterally across the fracture alignment device.

Alternatively, the alignment retainer may comprise a plurality of beads or pellets loosely disposed within the fluid tight chamber when at or about atmospheric pressure and tightly packed together when a vacuum is created within the fluid tight chamber by the fluid pressure regulator. When tightly packed under vacuum, the beads or pellets form a rigid mass such that the fracture alignment device immobilizes the patient's limb.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE INVENTION

The present invention relates to a fracture alignment device to immobilize a patient's limb PL without the necessity of using straps while allowing access to a surgical site during a surgical procedure. As described hereinafter, the fracture alignment device comprises two flexible layers of fluid impervious material cooperatively forming a fluid tight enclosure or chamber coupled to a pressure regulator to control the pressure within the fluid tight chamber in combination with an alignment retainer to position and maintain one of the flexible layers of fluid impervious material in contact with the patient's limb PL.

In addition, a plurality of fluid tight enclosures or chambers can be assembled together to engage a number of anatomical regions of a patient as a resuscitation bed or platform. The fluid tight enclosure or chambers can be controlled independently so the anatomical regions can be individually controlled to selectively function as a tourniquet to stop bleeding in a particular anatomical region. In addition, warm or cool fluid may be fed to one or more of the fluid tight chambers to warm or cool a patient.

The alignment retainer may comprise an endoskeleton pliable or malleable metal or formable thermoplastic in the form of a frame, sheet or slats or a plurality of beads, pellets or similar relatively small particulate material. As described hereinafter, the pressure regulator may comprise a positive pressure pump device or a vacuum pump device to create a pressure differential between the ambient atmosphere and the interior fluid tight enclosure or chamber depending on the type of alignment retainer employed.

Figure 1:
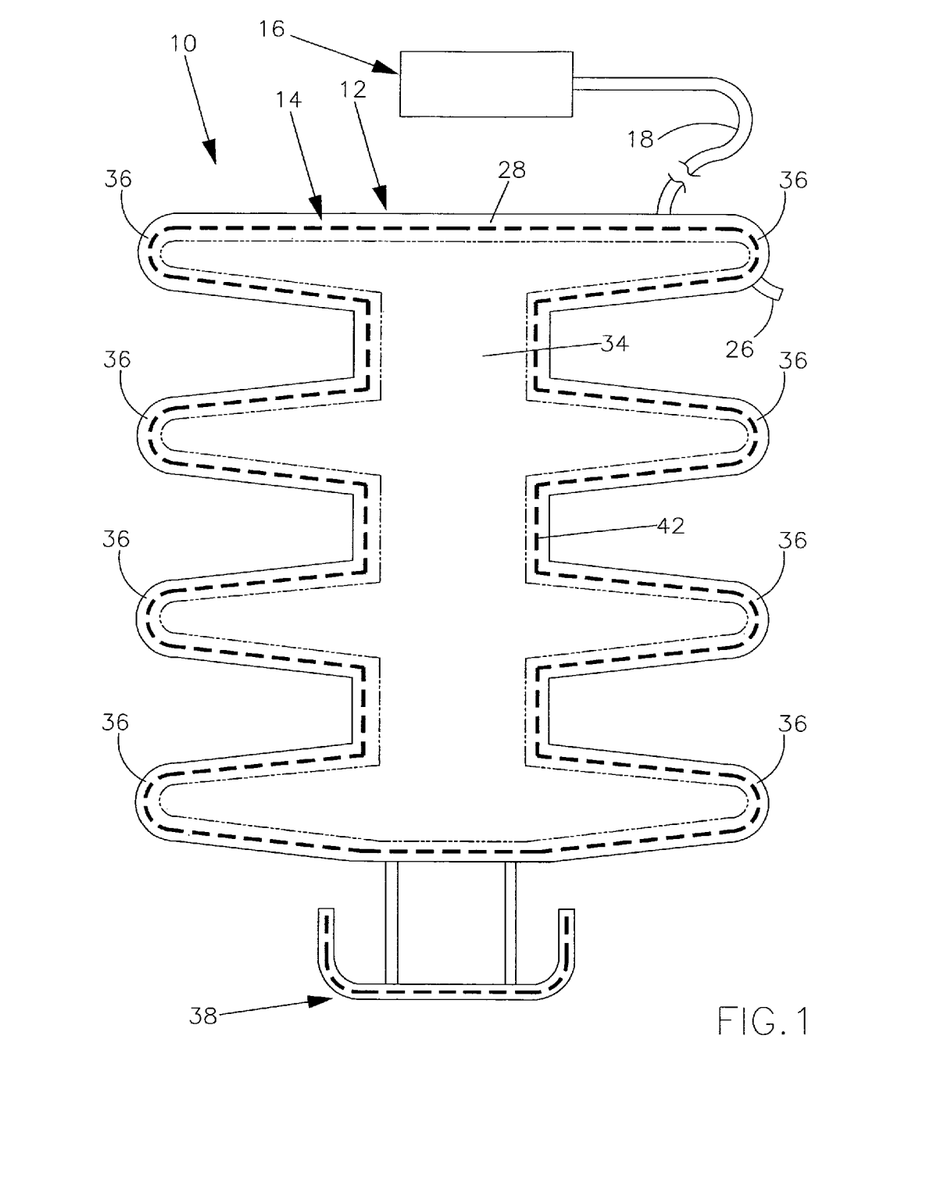
FIG. 1 is a front view of the fracture alignment device of the present invention with the inflatable fluid tight enclosure in the ambient state.
Figure 2:
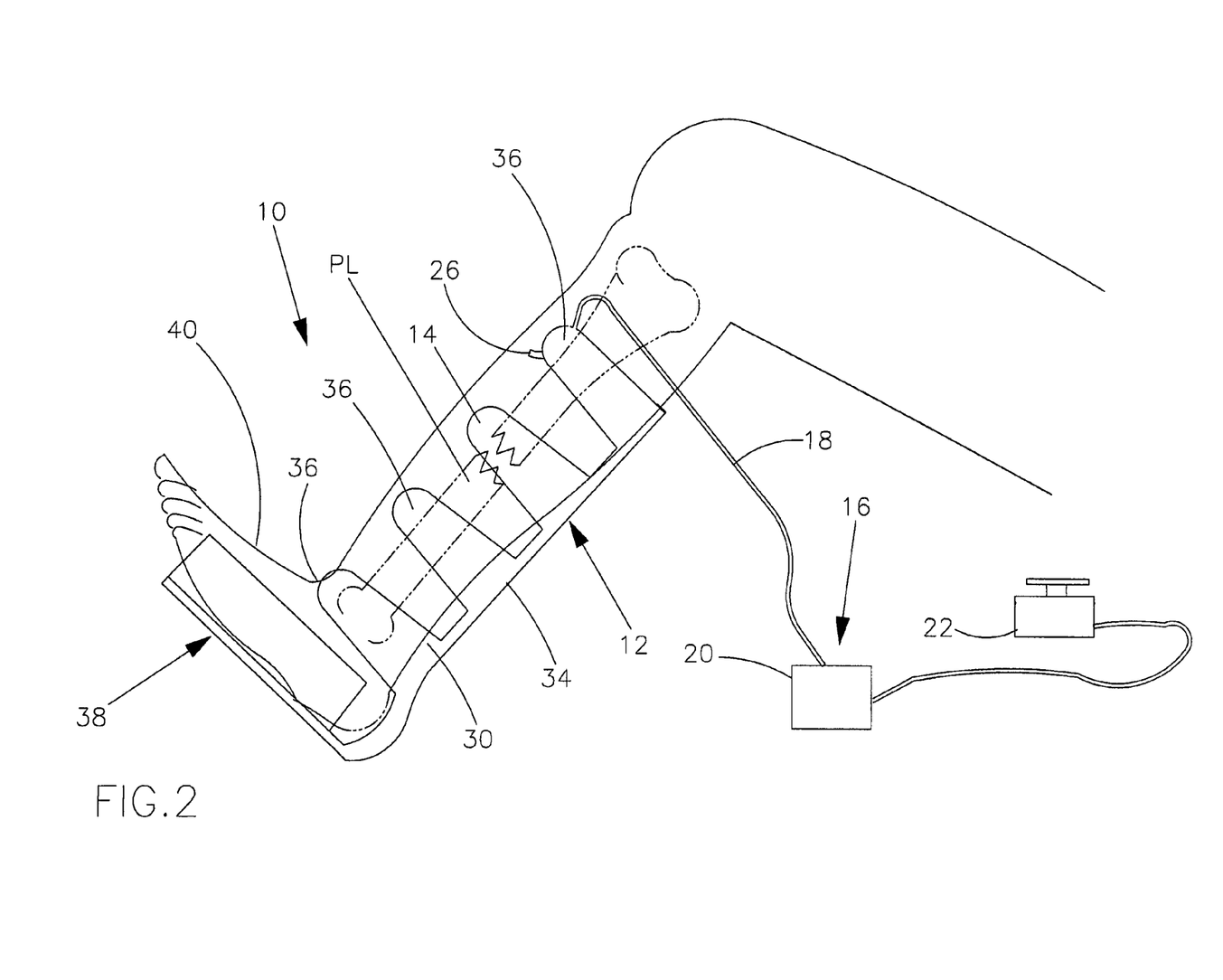
FIG. 2 is a side view of the fracture alignment device of the present invention with the inflatable fluid tight enclosure inflated around a patient's leg to immobilize the patient's leg.
Figure 3:
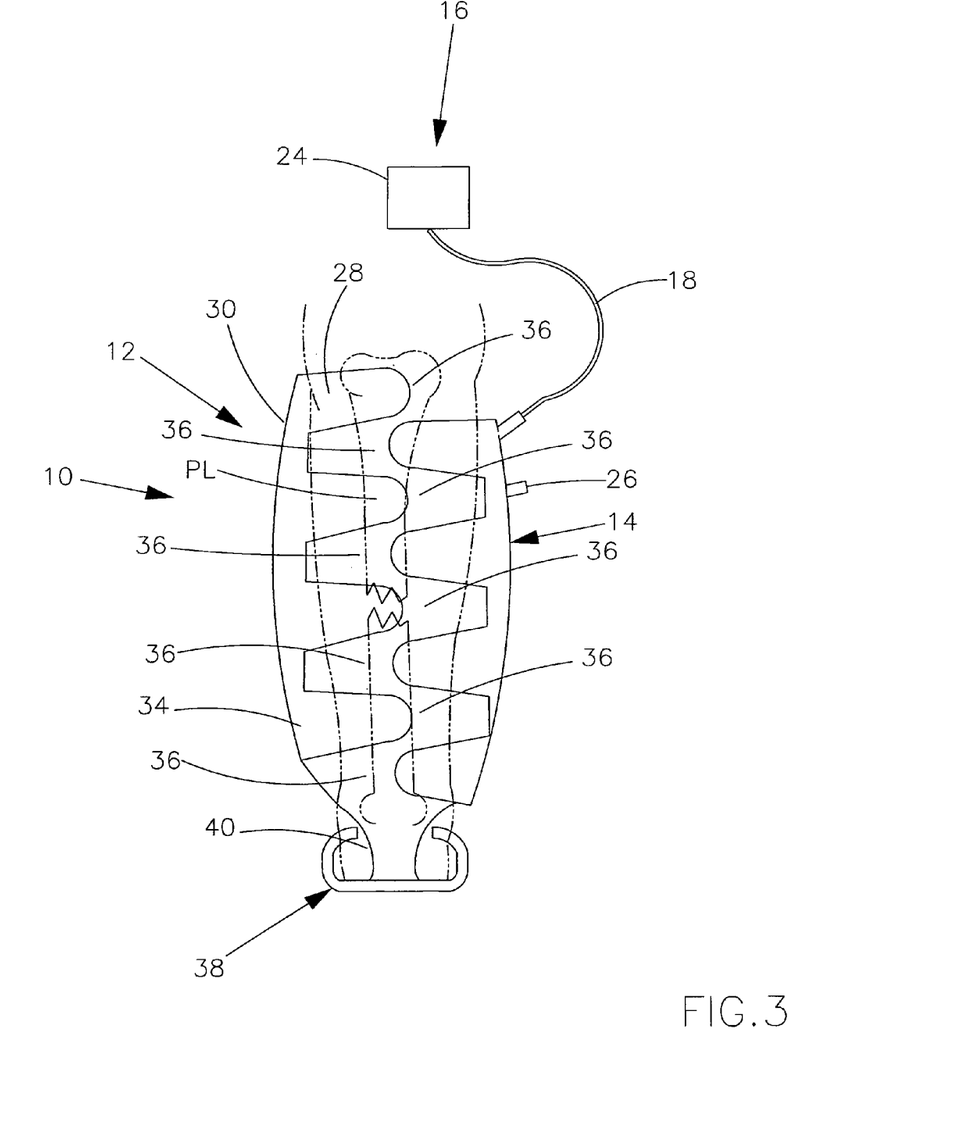
FIG. 3 is a front view of the fracture alignment device of the present invention with the inflatable fluid tight enclosure inflated around a patient's leg to immobilize the patient's leg.

FIGS. 1 through 3 depict a fracture alignment device generally indicated as 10 comprising an inflatable fluid tight enclosure or bladder generally indicated as 12 and an alignment retainer generally indicated 14.

The inflatable fluid tight enclosure or bladder 12 is coupled to a fluid pressure regulator generally indicated as 16 through a fluid supply conduit 18 to supply fluid to the interior of the inflatable fluid tight enclosure or bladder 12 to selectively inflate the inflatable fluid tight enclosure or bladder 12. The fluid pressure regulator 16 may comprise an air or gas pump or pressurized air or gas tank 20 with a control pedal 22 or similar air supply control (FIG. 2) or a manual air bulb 24 (FIG. 3) and a pressure relief valve 26 to selectively relieve the internal pressure from the interior of the inflatable fluid tight enclosure or bladder 12 to deflate the inflatable fluid tight enclosure or bladder 12 after use into an ambient state or condition. Although an air or gas source is generally envisioned, a liquid source (not shown) may be used to pressurize or inflate the inflatable fluid tight enclosure or bladder 12.

Figure 4:
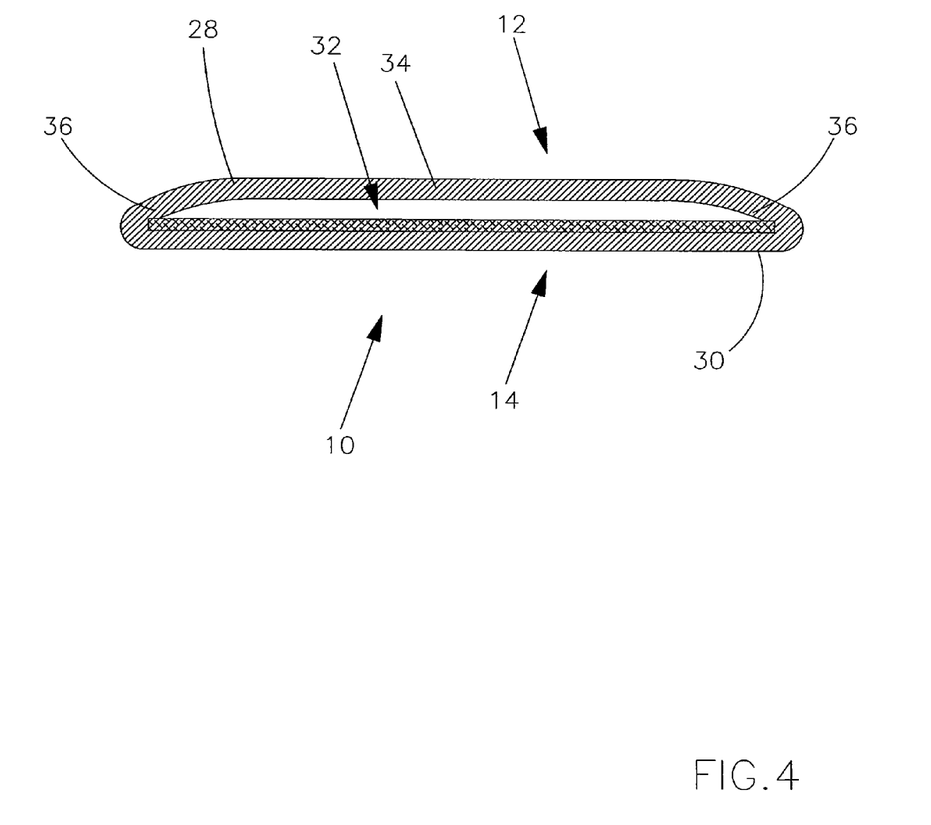
FIG. 4 is a cross-sectional view of the inflatable fluid tight enclosure or bladder of the present invention.

As best shown in FIG. 4, the inflatable fluid tight enclosure or bladder 12 comprises a first or inner flexible layer 28 and a second or outer flexible layer 30 of fluid impervious material sealed around the periphery thereof to cooperatively form a fluid tight chamber 32.

As shown in FIGS. 1 through 3, the first or inner flexible layer 28 and the second or outer flexible layer 30 each comprises a central major portion or body 34 having a plurality of lateral retainer extensions or fingers each indicated as 36 extending outwardly therefrom to engage and immobilize the patient's limb PL when the inflatable fluid tight enclosure or bladder 12 is inflated or in an immobilization state or condition. The lower end portion of the inflatable fluid tight enclosure or bladder 12 may terminate in a cup-like shape 38 to receive the foot and heel 40 of the patient to control or limit the movement of the foot and heel 40.

As shown in FIGS. 2 and 3, the central major portion of body 34 is substantially parallel to the patient's limb PL when placed on the patient. As shown in FIG. 1, each lateral retainer extension or finger 36 is substantially perpendicular to the central major portion or body 34.

The lateral retainer extensions or fingers 36 may be offset relative to each other as depicted in FIG. 3. More specifically, the lateral retainer extension or fingers on the first side of the major portion or body are aligned with the longitudinal opening formed between adjacent lateral retainer extensions or fingers on the second side of the major portion or body and the lateral retainer extensions or fingers on the second side of the central major portion or body are aligned with the longitudinal opening formed between adjacent lateral retainer extensions or fingers found on the first side of the central major portion or body.

As shown in FIG. 1, the alignment retainer 14 comprises a pliable or malleable wire-like element 42 of metal or other suitable material that can be bent or formed to follow the contour of the patient's limb PL to at least partially encircle the patent's limb PL in an operative position such that the central major portion or body 34 and the lateral retainer extensions or fingers 36 are held in position to engage the patient's limb PL when the inflatable fluid tight enclosure or bladder 12 is inflated with a gas, liquid or gel to immobilize the patient's limb PL. Of course, the alignment retainer 14 may comprise a plate or sheet 44 of pliable or malleable material as shown in FIG. 5 or a plurality of strips, slats or ribs each indicated as 46 of pliable or malleable material extending transversely or laterally across the fracture alignment device 10 as shown in FIG. 6.

Figure 7:
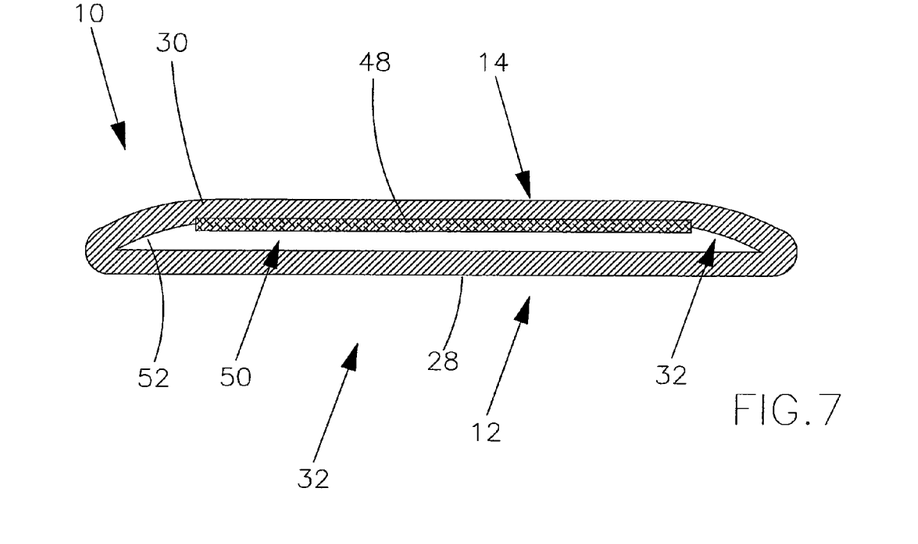
FIG. 7 is a cross-sectional view of the fracture alignment device of the present invention with yet another alternative embodiment of the alignment retainer.

Alternatively, as shown in FIG. 7, the alignment retainer 14 may comprise a thermoplastic material 48 disposed within a pocket 50 generally parallel with the inflatable fluid tight enclosure or bladder 12. The pocket 50 is formed by the space between the second or outer flexible layer 30 of fluid impervious inflatable fluid tight enclosure or bladder 12 and a third flexible layer 52 of material. The thermoplastic material 48 can comprise any suitable thermoplastic material such as polystyrene or polyethylene substantially rigid or hard at room or ambient temperature but flexible or soft when heated. The thermoplastic sheet or plate 48 is sized and shaped to flex or bend to the desired shape or contour when heated and retain the shape or contour when cooled to near room temperature. When cooled the sheet or plate 48 hardens to maintain the contour of the fracture alignment device 10 to immobilize the patient's limb PL.

Figure 5:
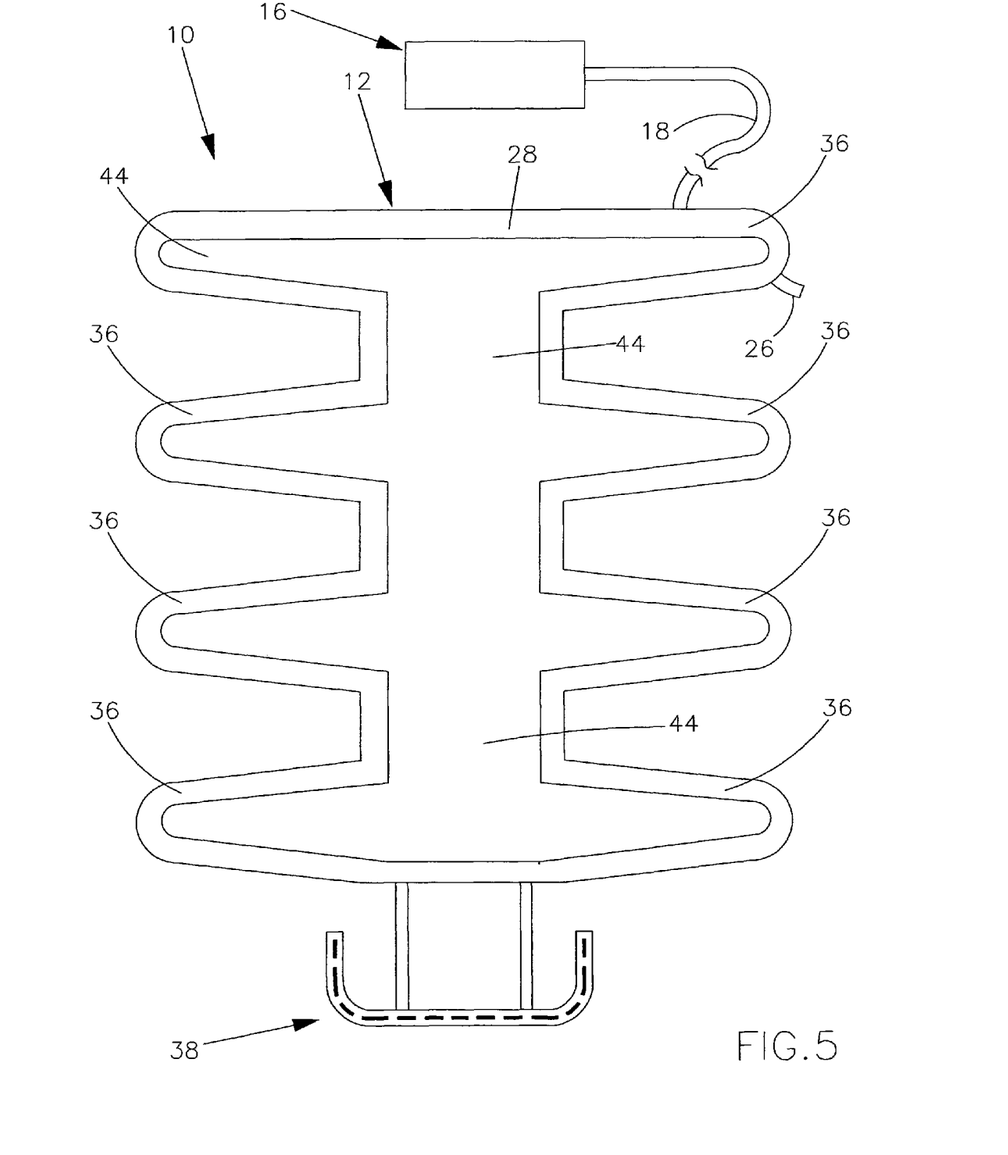
FIG. 5 is a front view of the fracture alignment device of the present invention with an alternative embodiment of the alignment retainer and the inflatable fluid tight enclosure in the ambient state.
Figure 6:
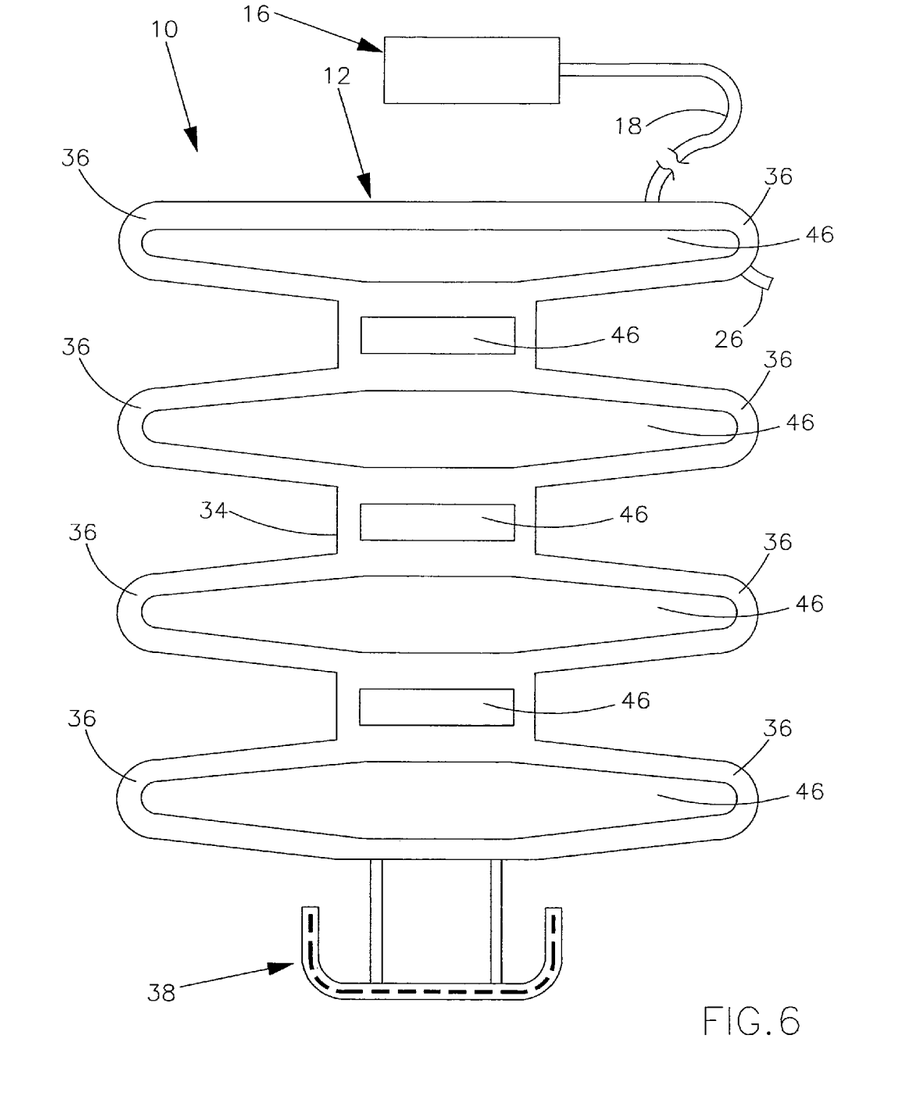
FIG. 6 is a front view of the fracture alignment device of the present invention with another alternative embodiment of the alignment retainer and the inflatable fluid tight enclosure in the ambient state.

As with the alignment retainer 14 pliable or malleable material shown in FIGS. 1, 5 and 6, the alignment retainer of thermoplastic material 48 may comprise a wire-like element, a plate or sheet or a plurality of strips, slats or ribs that can be bent or formed to follow the contour of the patient's limb PL to at least partially encircle the patent's limb PL in an operative position such that the central major portion or body 34 and the lateral retainer extensions or fingers 36 are held in position to engage the patient's limb PL when the inflatable fluid tight enclosure or bladder 12 is inflated with a gas, liquid or gel to immobilize the patient's limb PL.

Figure 8:
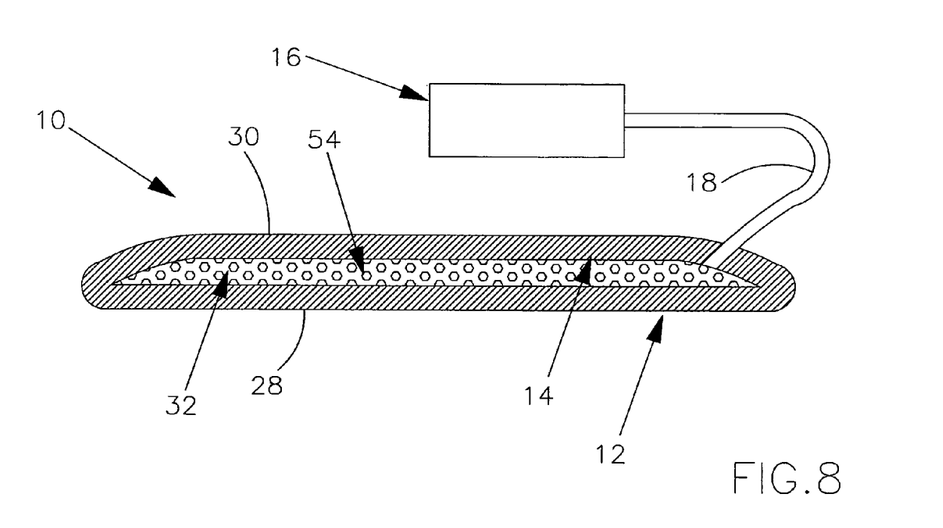
FIG. 8 is a cross-sectional view of an alternative embodiment of the fracture alignment device of the present invention in the ambient state.

FIG. 8 depicts another alternate embodiment of the alignment retainer 14 comprising a plurality of beads or pellets generally indicated as 54 loosely disposed within the fluid tight chamber 32 when at or about atmospheric pressure. The beads or pellets 54 are manufactured from a suitable material to permit the beads or pellets 54 to be tightly packed together when a vacuum is created within the fluid tight chamber 32 by the fluid pressure regulator 16.

Figure 9:
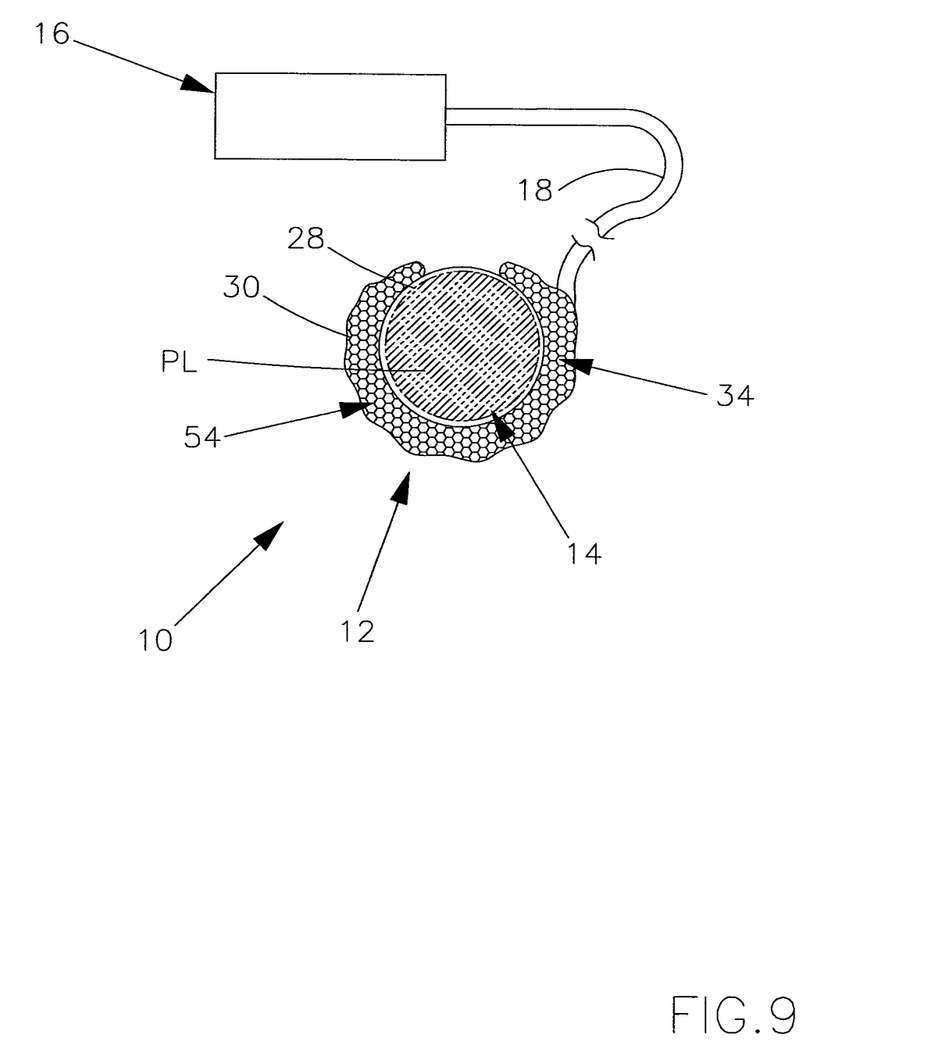
FIG. 9 is a cross-sectional end view of the alternative embodiment of the fracture alignment device of the present invention shown in FIG. 8 in the immobilization state to immobilize the patient's limb.

As shown in FIG. 9, when tightly packed under vacuum the beads or pellets 54 form a rigid mass such that the fracture alignment device 10 immobilizes the patient's limb PL.

Figure 10:
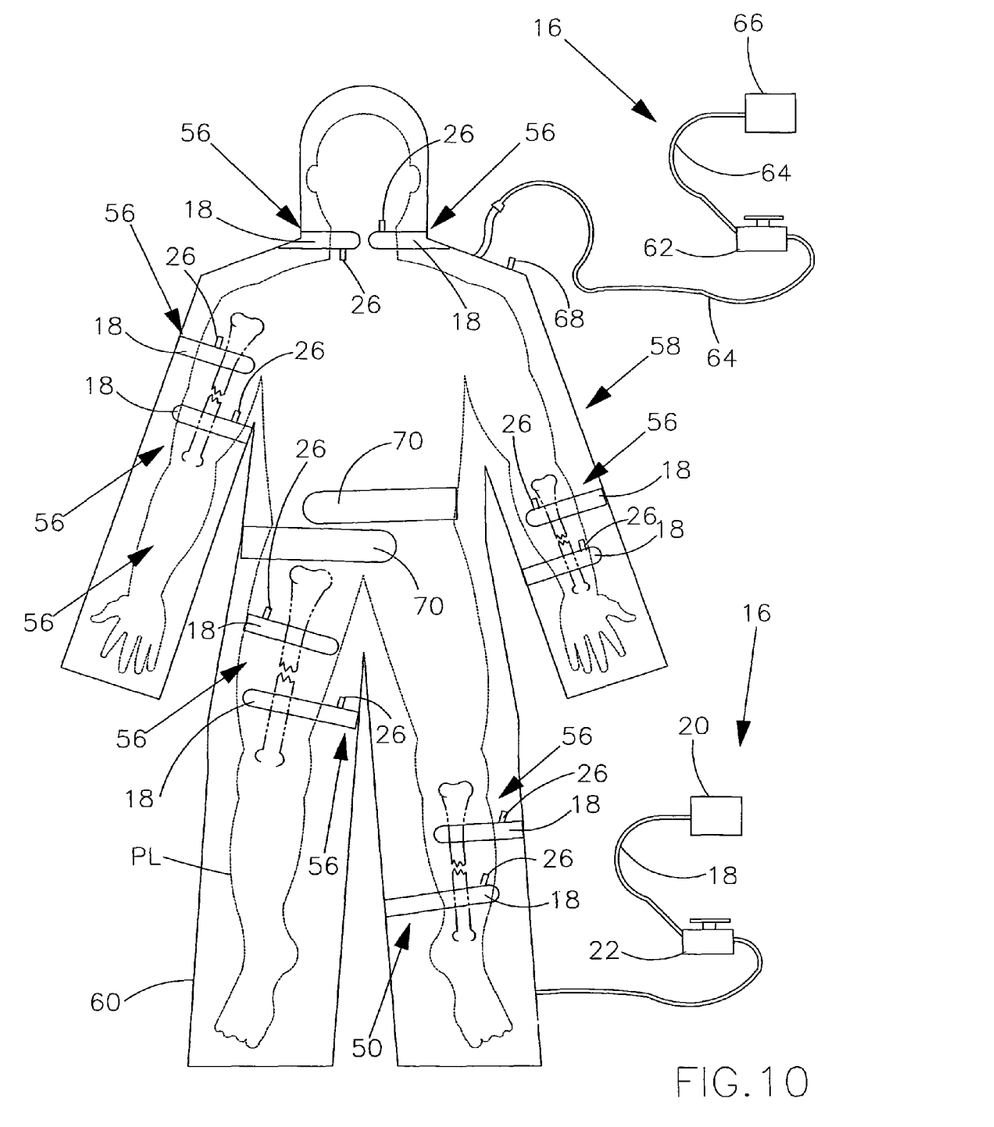
FIG. 10 is a top view of another alternate embodiment of the present invention comprising a resuscitation bed or platform.

Finally, as shown in FIG. 10, the present invention may comprise a plurality of inflatable retainer devices each generally indicated as 56 and a bed or platform generally indicated as 58. These inflatable retainer devices 56 are configured to engage the leg, the foot, the ankle, and the heel of a person. Each inflatable retainer device 56 is constructed similar to the fracture align device 10 depicted in FIGS. 1 through 6. That is, each inflatable retainer device 56 comprises an inflatable fluid tight enclosure or bladder and an alignment retainer. Each inflatable fluid tight enclosure or bladder is coupled to a fluid pressure regulator 16 through a fluid supply conduit 18 to supply fluid to the interior of the inflatable fluid tight enclosure or bladder to selectively inflate the individual inflatable fluid tight enclosures or bladders. The fluid pressure regulator 16 may comprise an air or gas pump or pressurized air or gas tank 20 with a control or similar air supply control. A pressure relief valve 26 may be used to selectively relieve the internal pressure from the interior of the individual inflatable fluid tight enclosures or bladders or the bed or platform 58 to deflate the inflatable fluid tight enclosure or bladder or the bed or platform 58 after use into an ambient state or condition. Each inflatable fluid tight enclosure or bladder 56 and the bed or platform 58 may have a one-way check valve (not shown) to prevent deflation of any other fluid tight enclosures or bladders 56 or the bed or platform 58 when deflating any particular chamber.

The inflation and pressure relief of the individual inflatable fluid tight enclosures or bladders creates the desired stiffness of the inflatable retainer devices 56 around the patient's limb PL so that the needed support is maintained and the movement and flexibility of the patient's limb PL is controlled without causing unnecessary discomfort. Moreover, the pressure created does not obstruct blood flow. When inflated, the inflatable retainer devices 56 conform to the shape of the appropriate portion of the body.

The bed or platform 58 may comprise an inflatable bed or mattress 60 coupled to a separate air pressure source 62 through a gas supply conduit 64 to feed gas to the interior of the bed or platform 58 when activated by a control 66. Pressure is relieved through valve 68.

Straps or belts 70 may be used to aid in securing the patient in place on the inflatable bed or mattress 60 or bed or platform 58.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

The invention claimed is:

1. An inflatable fracture alignment device to immobilize a patient's limb during a surgical procedure comprising an inner flexible layer and an outer flexible layer of fluid impervious material to cooperatively form a fluid tight chamber coupled to a pressure regulator to supply gas to said fluid tight chamber and an alignment retainer, said inner flexible layer and said outer flexible comprise an inflatable central major portion or body having a first lateral side and a second lateral side adapted to be disposed substantially parallel to the patient's limb to be immobilized and a plurality of inflatable lateral retainer extensions or fingers integrally formed with said inflatable central major portion or body adapted to be disposed substantially perpendicular to the patient's limb to be immobilized and to secure said inflatable fracture alignment device to the patient's limb, each said inflatable lateral retainer extension or finger extending outwardly from either said first lateral side of said inflatable central major portion or body or from said second lateral side of said central inflatable major portion or body, each said inflatable lateral retainer extension or finger having an outer periphery, said plurality of inflatable lateral retainer extensions or fingers on said first lateral side of said central inflatable major portion or body are spaced apart relative to each other to cooperatively form a longitudinal opening between adjacent inflatable lateral retainer extensions or fingers and said plurality of inflatable lateral retainer extensions or fingers on said second lateral side of said inflatable central major portion or body are spaced apart relative to each other to cooperatively form a longitudinal opening between adjacent inflatable lateral retainer extensions or fingers and said alignment retainer comprises a malleable wire element forming a continuous loop disposed adjacent said outer periphery of each said inflatable lateral retainer extension or finger to encircle at least most of the patient's limb when bent to conform with the patient's limb to secure said inflatable fracture alignment device on the patient's limb such that said inflatable central major portion or body and said inflatable lateral retainer extensions or fingers are held in position to immobilize the patient's limb during a surgical procedure and allow for normal blood flow when said inflatable fracture alignment device is inflated.

2. The inflatable fracture alignment device of claim 1 wherein adjacent portions of the malleable wire element on each lateral side of said inflatable central major portion or body are coupled together in spaced relationship relative to each other by a corresponding wire element disposed adjacent each corresponding lateral side of said inflatable central major portion or body adapted to be disposed substantially parallel to the patient's limb.

3. The inflatable fracture alignment device of claim 2 wherein said inflatable lateral retainer extensions or fingers on said first lateral side of said inflatable central major portion or body are aligned with said longitudinal openings formed between adjacent inflatable lateral retainer extensions or fingers on said second lateral side of said central major portion or body and said inflatable lateral retainer extensions or fingers on said second lateral side of said inflatable central major portion or body are aligned with said longitudinal openings formed between adjacent inflatable lateral retainer extensions or fingers of said first lateral side of said inflatable central portion or body.

4. The inflatable fracture alignment device of claim 1 wherein said inflatable lateral retainer extensions or fingers on said first lateral side of said inflatable central major portion or body extend into said longitudinal openings formed between adjacent inflatable lateral retainer extensions or fingers on said second lateral side of said inflatable central major portion or body and said inflatable lateral retainer extensions or fingers on said second lateral side of said inflatable central major portion or body extend into said longitudinal openings formed between adjacent inflatable lateral retainer extensions or fingers of said first lateral side of said inflatable central portion or body in use such that said inflatable fracture alignment device is adapted to substantially encircle the patient's limb to secure said inflatable fracture alignment device on the patient's limb.

5. An inflatable fracture alignment device to immobilize a patient's limb during a surgical procedure comprising an inner flexible layer and an outer flexible layer of fluid impervious material to cooperatively form a single fluid tight chamber coupled to a pressure regulator to supply gas to said fluid tight chamber and an alignment retainer, said inner flexible layer and said outer flexible layer comprise an inflatable central major portion or body extending substantially the longitudinal length of said inflatable fracture alignment device, said inflatable central major portion or body having a first lateral side and a second lateral side adapted to be disposed substantially parallel to the patient's limb to be immobilized and a plurality of inflatable lateral retainer extensions or fingers integrally formed with said inflatable central major portion or body adapted to be disposed substantially perpendicular to the patient's limb to be immobilized, each said inflatable lateral retainer extension or finger extending outwardly from either said first lateral side of said inflatable central major portion or body or from said second lateral side of said inflatable central major portion or body, each said inflatable lateral retainer extension or finger having an outer periphery, said plurality of inflatable lateral retainer extensions or fingers on said first lateral side of said inflatable central major portion or body are spaced apart relative to each other to cooperatively form a longitudinal opening between adjacent inflatable lateral retaining extensions or fingers and said plurality of inflatable lateral retainer extensions or fingers on said second lateral side of said inflatable central major portion or body are spaced apart relative to each other to cooperatively form a longitudinal opening between adjacent inflatable lateral retainer extensions or fingers and said alignment retainer comprises a malleable wire element forming a continuous loop disposed adjacent said outer periphery of each said inflatable lateral retainer extension or finger to conform to the patient's limb when bent to secure said inflatable fracture alignment device on the patient's limb and wherein said inflatable lateral retainer extensions or fingers on said first lateral side of said inflatable central major portion or body extend into said longitudinal openings formed between adjacent inflatable lateral retainer extensions or fingers on said second lateral side of said inflatable central major portion or body and said inflatable lateral retainer extensions or fingers on said second lateral side of said inflatable central major portion or body extend into said longitudinal openings formed between adjacent inflatable lateral retainer extensions or fingers of said first lateral side of said inflatable central portion or body in use such that said fracture alignment device is adapted to substantially encircle the patient's limb such that said inflatable central major portion or body and said inflatable lateral retainer extensions or fingers are held in position to immobilize the patient's limb during a surgical procedure and allow for normal blood flow when said inflatable fracture alignment device is inflated.

* * * * *